US011369367B2

(12) United States Patent
Mizutani et al.

(10) Patent No.: US 11,369,367 B2
(45) Date of Patent: Jun. 28, 2022

(54) SUTURING DEVICE

(71) Applicant: ZEON CORPORATION, Tokyo (JP)

(72) Inventors: Kyoichiro Mizutani, Tokyo (JP); Kohei Sakaki, Tokyo (JP); Koichi Inoue, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 167 days.

(21) Appl. No.: 16/482,239

(22) PCT Filed: Jan. 31, 2018

(86) PCT No.: PCT/JP2018/003146
§ 371 (c)(1),
(2) Date: Jul. 30, 2019

(87) PCT Pub. No.: WO2018/143248
PCT Pub. Date: Aug. 9, 2018

(65) Prior Publication Data
US 2020/0000459 A1    Jan. 2, 2020

(30) Foreign Application Priority Data
Jan. 31, 2017 (JP) .............................. JP2017-015931

(51) Int. Cl.
*A61B 17/062* (2006.01)
*A61B 17/04* (2006.01)

(52) U.S. Cl.
CPC ........ *A61B 17/062* (2013.01); *A61B 17/0469* (2013.01); *A61B 17/0482* (2013.01); *A61B 17/0483* (2013.01)

(58) Field of Classification Search
CPC ...... A61B 2017/06052; A61B 17/0482; A61B 17/0491; A61B 17/0483; A61B 17/0625; A61B 17/06109; A61B 17/062
See application file for complete search history.

(56) References Cited

U.S. PATENT DOCUMENTS 9,579,096 B2 *   2/2017   Mori .................. A61B 17/0483
2017/0245852 A1   8/2017   Kim

FOREIGN PATENT DOCUMENTS

EP           2668909 A1    12/2013
JP        2010-136733 A     6/2010
(Continued)

OTHER PUBLICATIONS

Extended European Search Report dated Jul. 13, 2020, issued in EP 18747833.4.
(Continued)

*Primary Examiner* — Wade Miles
*Assistant Examiner* — Mohammed S Adam
(74) *Attorney, Agent, or Firm* — Knobbe, Martens, Olson & Bear, LLP

(57) ABSTRACT

A suturing device for being inserted into and used in a body is disclosed. The suturing device includes a front arm that has string support portions supporting both ends of a surgical string, and a front guide portion attached to the string support portions and a back arm that has a needle-shaped member, a needle support portion supporting the needle-shaped member in a state of pointing to a predetermined first direction, and a back guide portion attached to the front guide portion such that the back guide portion is capable of sliding in a direction substantially parallel to the first direction, and rotating around an axis substantially parallel to the first direction. The front guide portion has a first guide groove guiding the needle-shaped member to one end of the surgical string supported by the string support portion and a second guide groove guiding the needle-shaped member.

4 Claims, 15 Drawing Sheets

(56) References Cited

FOREIGN PATENT DOCUMENTS

| | | |
|---|---|---|
| JP | 2017-169941 A | 9/2017 |
| WO | WO 01/67963 A2 | 9/2001 |
| WO | WO 2012/101999 A1 | 8/2012 |
| WO | WO 2016/080640 A1 | 5/2016 |

OTHER PUBLICATIONS

Notification of Transmittal of Translation of the International Preliminary Report on Patentability received in connection with International Patent Application No. PCT/JP2018/003146 dated Aug. 15, 2019.

International Search Report received in International Patent Application No. PCT/JP2018/003146 dated Apr. 10, 2018.

\* cited by examiner

SUTURING DEVICE

TECHNICAL FIELD

The present invention relates to a suturing device for suturing an incised site or the like formed in an internal body tissue of the digestive tract or the like in natural orifice translumenal endoscopic surgery.

BACKGROUND ART

In recent years, medical practitioners pay attention to natural orifice translumenal endoscopic surgery (NOTES) as non-invasive surgery in which no cut is made in the body skin. Unlike surgery in the related art in which an operator incises the body skin and brings a treatment tool to a target lesion in a body cavity, the operator brings the treatment tool to the target lesion from a natural ostium, for example, the mouth, the anus, the urethral opening or the vaginal opening, through the digestive tract, the urethra, or the birth canal using an endoscope. It is reported that the natural orifice translumenal endoscopic surgery can be applied to a variety of procedures, from diagnostic procedures such as observation of the abdominal cavity, and liver biopsy to procedures such as appendectomy, cholecystectomy, tubal ligation, ovariectomy, and gastroenterostomy.

Patent Document 1 discloses a suture device for suturing an incised site (including a perforated site, a defective site, and the like), which is formed in an internal body tissue of the digestive tract or the like, in the natural orifice translumenal endoscopic surgery. The suture device includes a front arm having bifurcated tip portions, on which a surgical string is mounted across between the tip portions; a back arm having a puncture needle; and a mechanism for rotating and moving the front and back arms relative to each other.

Incidentally, when suturing the incised site using the suture device, an operator requires to set the rotational position of the back arm with respect to that of the front arm such that the needle accurately coincides with each of the bifurcated tip portions (portions supporting both ends of the surgical string) of the front arm, and thereafter to move the back arm close to the front arm. However, in the related art, when the back arm is brought close to the front arm, the rotational position of the back arm may be misaligned with that of the front arm. For this reason, position realignment or the like may be required, thereby becoming an obstacle to prompt treatment, and it is necessary to improve the problem.

CITATION LIST

Patent Document

Patent Document 1: WO 2012/101999 A

SUMMARY OF THE INVENTION

Problem to be Solved by the Invention

The invention is made in light of the problem, and an object of the invention is to provide a suturing device for suturing an internal body tissue in a short period of time.

Means for Solving Problem

According to the invention, in order to achieve the object, there is provided a suturing device for being inserted into and used in a body, the device including a front arm having a string support portion supporting both ends of a surgical string, and a front guide portion attached to the string support portion; and a back arm having a needle-shaped member, a needle support portion supporting the needle-shaped member in a state of pointing to a predetermined first direction, and a back guide portion attached to the front guide portion such that the back guide portion is capable of sliding in a direction substantially parallel to the first direction, and rotating around an axis substantially parallel to the first direction, in which the front guide portion has a first guide groove guiding the needle-shaped member to one end of the surgical string supported by the string support portion, and a second guide groove guiding the needle-shaped member to the other end of the surgical string, when the back arm slides in the first direction.

In the invention, if the back arm slides in the first direction (direction in which the back arm becomes close to the front arm), the first guide groove guides the needle-shaped member to one end of the surgical string supported by one string support portion, and the second guide groove guides the needle-shaped member to the other end of the surgical string supported by the other string support portion. As a result, when the back arm is brought close to the front arm, the rotational position of the back arm is effectively prevented from being misaligned with that of the front arm. For this reason, there is no need to realign the positions as in the related art, and it is possible to promptly perform suture treatment.

In the invention, the front guide portion may have substantially a tubular member, the first guide groove and the second guide groove may have guide through-grooves which extend in the direction substantially parallel to the first direction, and which are formed in a wall portion of the front guide portion such that the guide through-grooves extend from an inside to an outside, the back guide portion may be disposed inside the front guide portion, and the needle support portion may be slidably and freely fitted into the guide through-grooves. It is possible to accurately align the position of the needle-shaped member with those of both ends of the surgical string owing to such simple configuration employed.

Further, in the invention, the front guide portion may have substantially a tubular member, the first guide groove and the second guide groove may have recessed guide grooves which extend in the direction substantially parallel to the first direction, and which are formed in an inner wall of the front guide portion, the back guide portion may be disposed inside the front guide portion, and the back guide portion may be provided with a projection portion that is freely fitted into the recessed guide grooves. It is possible to accurately align the position of the needle-shaped member with those of both ends of the surgical string owing to such simple configuration employed.

In the invention, a tying tool, which is capable of tying the surgical string with which an internal body tissue is sutured, may be mounted on the needle-shaped member.

MODE(S) FOR CARRYING OUT THE INVENTION

Hereinbelow, an embodiment of the invention will be described in detail with reference to the drawings.

(Entire Configuration of Suturing Device)

Figure 1A:
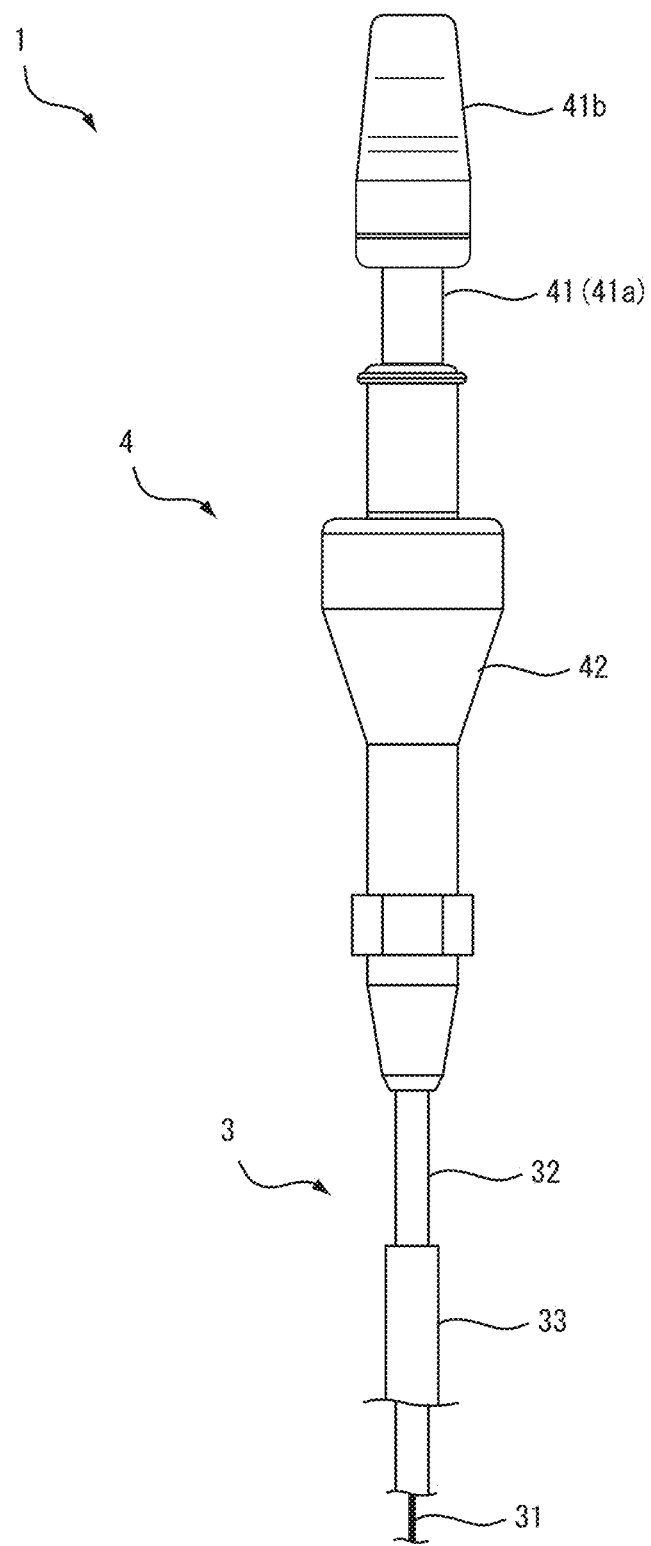
FIG. 1A is a front view illustrating a configuration of an operation unit of a suturing device in an embodiment of the invention.
Figure 1B:
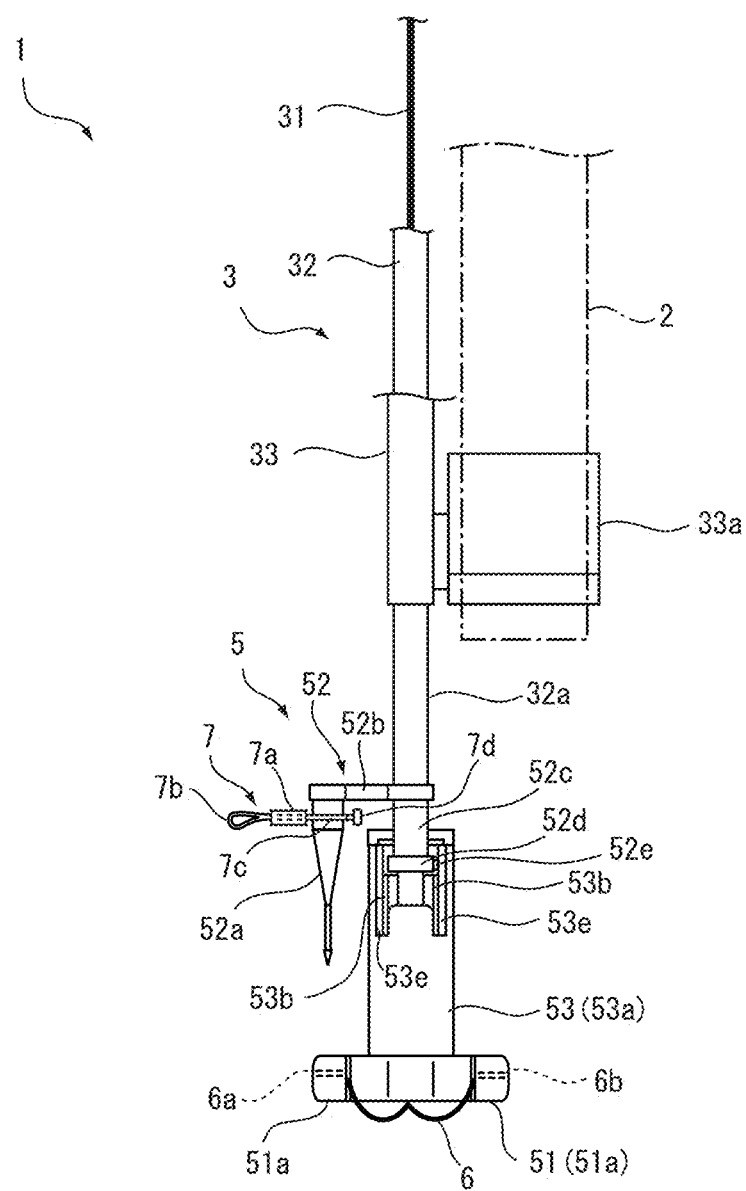
FIG. 1B is a front view illustrating a configuration of a suturing unit of the suturing device in the embodiment of the invention.

As illustrated in FIGS. 1A and 1B, a suturing device 1 of the embodiment is a device that allows an operator to suture an incised site or the like, which is formed in an organ or the digestive tract inside the abdominal cavity, by inserting the device into the body in a state where the device is attached to an endoscope (soft endoscope or the like) 2, and by operating the device outside the body while observing the incised site or the like using a camera (not illustrated) of the endoscope 2.

The suturing device 1 schematically includes a sheath unit 3 which is disposed along a shaft of the endoscope 2; an operation unit (handle) 4 which is provided at a proximal end of the sheath unit 3; and a suturing unit 5 which is provided at a distal end of the sheath unit 3.

(Sheath Unit)

The sheath unit 3 is an elongated member which extends along an axial direction. The sheath unit 3 includes two tubes and one wire (or three tubes) which have such flexibility that two tubes and one wire can be bent to follow the curvature of the shaft of the endoscope 2. That is, the sheath unit 3 schematically includes a front arm moving wire 31; a back arm moving tube 32; and a case tube 33.

The front arm moving wire 31 is made of a wire rod having plasticity. The front arm moving wire 31 is provided being slidably inserted into the back arm moving tube 32, and being capable of moving along an axial direction of the back arm moving tube 32, and rotating around an axis of the back arm moving tube 32 inside the back arm moving tube 32. In the embodiment, a wire rope is used as the front arm moving wire 31. The wire rope is a rope made of a stranded wire which is obtained by helically stranded together a plurality of metallic (stainless steel or the like) wires (cables). Here, a single wire may be used as the wire 31. Further, a hollow tube may be used instead of the wire 31.

The back arm moving tube 32 is a hollow tube which is slidably inserted into the case tube 33. The back arm moving tube 32 is provided capable of moving along an axial direction of the case tube 33, and rotating around an axis of the case tube 33 inside the case tube 33. A tube made of resin or the like and having plasticity may be used as the back arm moving tube 32. However, in the embodiment, a coil tube with a good durability is used as the back arm moving tube 32. It is possible to use as flat-wire coil tube, which is obtained by helically winding an elongated flat metallic (stainless steel or the like) sheet, as the coil tube. Here, a round-wire coil tube, or a coil tube with a flat inner surface may be used as the coil tube.

Incidentally, a wire tube may be used as the back arm moving tube 32. The wire tube is a tube which is obtained by helically stranded together, for example, a plurality of metallic (stainless steel or the like) wires (cables) to form a hollow tube.

The back arm moving tube 32 may be a member (for example, coil tube) which is uniform from a proximal end to a distal end thereof. However, in the embodiment, the back arm moving tube 32 has a tip portion (tip portion of tube) 32a which is obtained by fixing substantially a tubular member, which is made of metal and has a high rigidity, to the distal end of the coil tube via welding.

The case tube 33 is a hollow tube which is made of resin or the like and has plasticity. The respective proximal ends of the front arm moving wire 31 and the back arm moving tube 32 are connected to the operation unit 4. The respective distal ends of the front arm moving wire 31 and the back arm moving tube 32 are connected to the suturing unit 5. A proximal end of the case tube 33 reaches to the vicinity of the operation unit 4, but is not connected to the operation unit 4. A distal end of the case tube 33 reaches the vicinity of the suturing unit 5, but is not connected to the suturing unit 5. The case tube 33 can be formed of a material, for example, polyethylene or vinyl chloride.

A fixing member 33a having substantially a tubular shape is integrally attached to the distal end of the case tube 33. A tip portion of the shaft of the endoscope 2 is press-fitted into the fixing member 33a such that the suturing device 1 can be detachably fixed to the endoscope 2. It is possible to move the entirety of the suturing unit 5 with respect to the endoscope 2 by moving (sliding) the entirety of the operation unit 4 to a distal end side or a proximal end side with respect to the case tube 33. It is possible to rotate the entirety of the suturing unit 5 by rotating the entirety of the operation unit 4 around the axis of the case tube 33.

(Suturing Unit)

The suturing unit 5 of the suturing device 1 has a configuration as illustrated in FIG. 1B. That is, the suturing unit 5 includes a front arm 51 on which a surgical string 6 is mounted; and a back arm 52 having a needle-shaped member 52a.

Figure 2A:
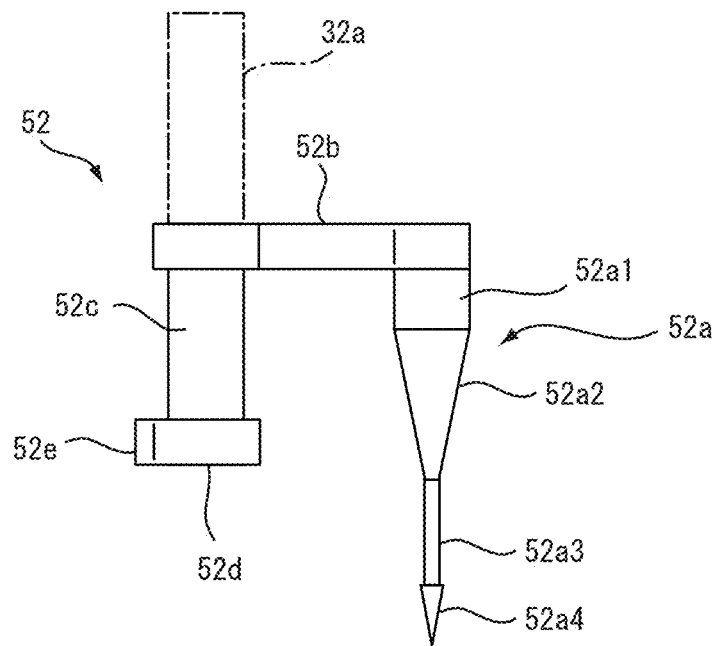
FIG. 2A is a front view of a back arm of the suturing unit illustrated in FIG. 1B.
Figure 2B:
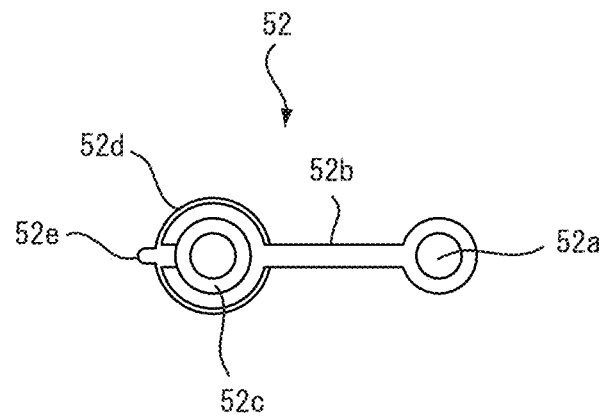
FIG. 2B is a plan view of the back arm illustrated in FIG. 2A.
Figure 3A:
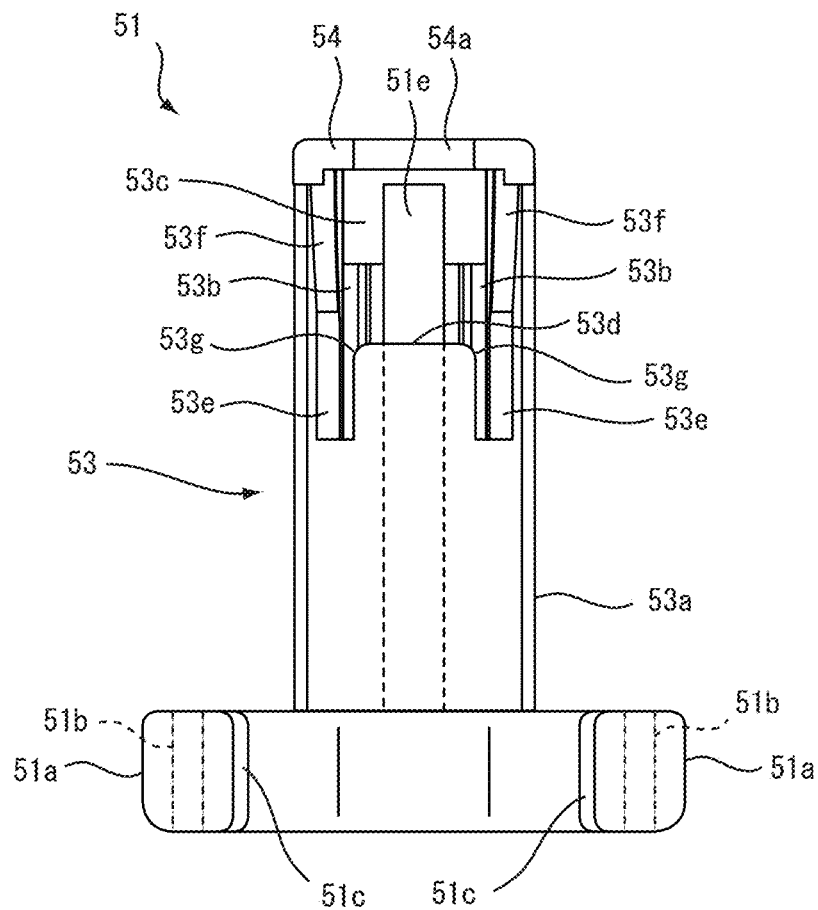
FIG. 3A is a front view of a front arm of the suturing unit illustrated in FIG. 1B.
Figure 3B:
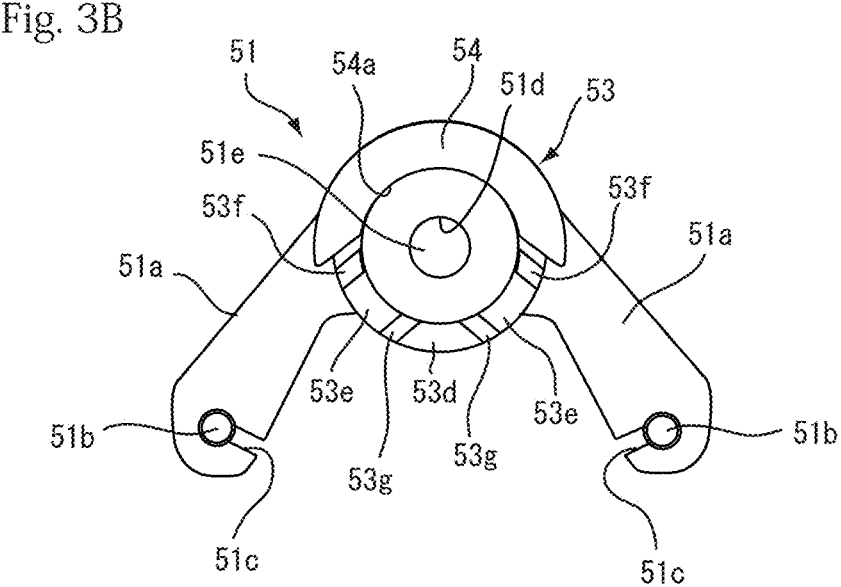
FIG. 3B is a plan view of the front arm illustrated in FIG. 3A.
Figure 3C:
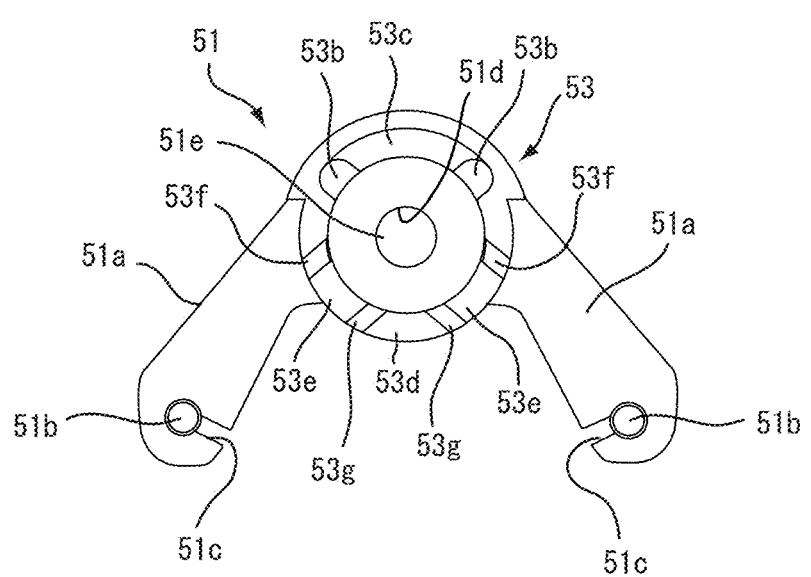
FIG. 3C is a plan view illustrating a case where a cap is detached from the front arm illustrated in FIG. 3B.

As illustrated in FIGS. 2A and 2B, the back arm 52 has the needle-shaped member 52a; a needle support portion 52b; a back guide portion 52c; and a projection member 52d. The back guide portion 52c is substantially a tubular member. One end of the needle support portion 52b having substantially a strip shape is fixed to an upper end of the back guide portion 52c, and the projection member 52d is fixed to a lower end of the back guide portion 52c.

A base end portion of the needle-shaped member 52a is fixed to the other end of the needle support portion 52b in a state where the needle-shaped member 52a points forward (to the distal end side). The projection member 52d has a projection portion 52e. The needle-shaped member 52a, the needle support portion 52b, the back guide portion 52c, and the projection member 52d are, but are not specifically limited to being, made of metal such as stainless steel, and are integrally fixed to each other via laser welding or the like after being formed as separate components. Incidentally, in the embodiment, the projection portion 52e is disposed projecting 180° opposite to an extending direction of the needle support portion 52b, but is not specifically limited to being disposed in this way.

In the back arm 52, a posterior end surface (end surface facing the proximal end side) of the back guide portion 52c is integrally fixed to the tip portion 32a of the back arm moving tube 32 via laser welding or the like (refer to FIG. 1B). The back guide portion 52c is inserted into a front guide portion 53 (will be described later), beginning from an end portion adjacent to the projection member 52d, and is held capable of sliding along an axial direction of the front guide portion 53, and rotating around an axis of the front guide portion 53.

The needle-shaped member 52a has a large-diameter portion 52a1 having a straight barrel shape; a tapered portion 52a2 with a narrow tip; a small-diameter portion 52a3 having a straight barrel shape; and an arrowhead portion 52a4 with a sharpened tip, which are disposed in sequence from a base to a tip of the needle-shaped member 52a. The arrowhead portion 52a4 is formed such that the outer diameter of a base of the arrowhead portion 52a4 is larger than the outer diameter of a tip of the small-diameter portion 52a3 and the arrowhead portion 52a4 is capable of having a slightly stepped part connected to the small-diameter portion 52a3. The needle-shaped member 52a is fixed to the needle support portion 52b such that a tip of the needle-shaped member 52a faces the front arm 51 and a central axis of the needle-shaped member 52a is substantially parallel to a central axis of the back guide portion 52c. Incidentally, a first direction is a central axis direction of the needle-shaped member 52a, and a direction from the base to the tip of the needle-shaped member 52a.

If rotating the back arm moving tube 32 around a central axis thereof, it is possible to rotate (orbit) the needle-shaped member 52a around a central axis of the tip portion 32a while maintaining that the central axis of the needle-shaped member 52a is substantially parallel to the central axis of the tip portion 32a.

Incidentally, the needle-shaped member 52a is capable of puncturing and passing through a suture target (internal body wall). Furthermore, the needle-shaped member 52a may have such length and strength that the needle-shaped member 52a can be moved in an opposite direction from a state where the needle-shaped member 52a has passed through the target, and pulled out of the target. The needle-shaped member 52a is not specifically limited to being made of a specific material, or having a specific length or axial diameter. For example, if the stomach wall is sutured using the suturing device 1, the needle-shaped member 52a may have such length that the needle-shaped member 52a is capable of passing through the stomach wall, and the material of the needle-shaped member 52a preferably is metal from a strength perspective. For example, the needle-shaped member 52a preferably has a length of approximately 7 to 20 mm, more preferably, approximately 7 to 10 mm. Further, in the needle-shaped member 52a, the large-diameter portion 52a1 has an axial diameter of approximately 1.5 to 3.0 mm, the small-diameter portion 52a3 has an axial diameter of approximately 0.5 to 1 mm, and the arrowhead portion 52a4 has a maximum axial diameter of approximately 0.6 to 1.5 mm.

As illustrated in FIG. 1B, a tying tool 7 for tying the surgical string 6 is mounted on the base end portion (large-diameter portion 52a1) of the needle-shaped member 52a. The tying tool 7 includes a main body portion which is formed by integrally providing a tying loop 7c (through which the surgical string 6 passes) at one axial end of a connection portion (which is substantially cylindrically formed), and by integrally providing a connection loop 7b (to which a tying device is connected) at the other axial end. In the tying tool 7, a tube (tightening tube) 7a, which is made of an elastic material and has substantially a tubular shape, is slidably fitted onto the connection portion. For tying, the tying loop 7c is pulled into a lumen of the tube 7a by sliding the tube 7a to the tying loop 7c. For example, polyamide resin is used as the material of the main body portion, and for example, silicone elastomer is used as the material of the tightening tube 7a.

Incidentally, in the embodiment, a latch member 7d for latching part of the tying loop 7c is provided, but is not specifically limited to being provided, in order to prevent the tying loop 7c from being excessively pulled into the tube 7a, and escaping from the tube 7a. Further, as the tying tool 7, there may be used a tool which is obtained by forming a loop member in substantially a loop shape (endless shape) by binding together both ends of a wire rod having plasticity, then by bringing middle portions of the loop member close to each other such that the middle portions are substantially parallel to each other, and then by slidably fitting the tube (tightening tube) 7a, which is made of an elastic material and has substantially a tubular shape, onto the middle portions.

As illustrated in FIG. 1B and FIGS. 3A to 3C, the front arm 51 schematically includes a pair of string support portions 51a and 51a; the front guide portion 53; and a cap 54. The pair of string support portions 51a and 51a is formed in a bifurcated shape, specifically, substantially V shape (may be arc shape, angular U shape, U shape, or the like). The surgical string 6 is mounted across between the vicinities of tip portions of the string support portions 51a and 51a. Engagement members 6a and 6b, which are annularly formed, are attached to both ends of the surgical string 6, respectively (refer to FIG. 1B).

Through-holes 51b and 51b are formed in the tip portions of the string support portions 51a and 51a of the front arm 51 in such a way as to pass through the tip portions from anterior surfaces (surfaces facing the distal end side) to posterior surfaces (surfaces facing the proximal end side) of the tip portions, respectively. Accommodation spaces (not illustrated) are formed in a posterior surface side of the through-holes 51b and 51b, which are adjacent to the posterior surfaces, and the engagement members 6a and 6b can be engaged into the accommodation spaces, respectively. Through-grooves 51c and 51c extending from the inside to the outside are formed in parts of side portions of the through-holes 51b and 51b such that the surgical string 6 is capable of passing through the through-grooves 51c and 51c, respectively. The accommodation spaces are set to have diameters which are slightly larger than the diameter of the through-holes 51b and 51b, specifically, to have such diameter that the engagement members 6a and 6b can be engaged with inner walls of the through-holes 51b and 51b of the string support portions 51a and 51a in a state where through-holes of the engagement members 6a and 6b, which pass therethrough from the tops to the bottoms thereof, are disposed substantially concentrically with the through-holes 51b and 51b.

The through-hole of each of the engagement members 6a and 6b has a structure in which the arrowhead portion 52a4 of the needle-shaped member 52a can be inserted into the through-hole, and if the arrowhead portion 52a4 is fully inserted into the through-hole, the engagement members 6a and 6b do not fall out of the needle-shaped member 52a. Specifically, each of the engagement members 6a and 6b is formed such that the inner diameter of each of the engagement members 6a and 6b is smaller than the outer diameter of the arrowhead portion 52a4 of the needle-shaped member 52a, and is larger than the axial diameter of the tip (that is, the part connected to the arrowhead portion 52a4) of the small-diameter portion 52a3 of the needle-shaped member 52a. Incidentally, a surgical string accommodation portion (not illustrated) is provided in a central portion of the string support portions 51a and 51a, and accommodates a middle part of the surgical string 6 disposed across between the string support portions 51a and 51a.

Incidentally, the front arm 51 may have a needle accommodation hole, but which is not provided in the embodiment, for protecting the needle-shaped member 52a (arrowhead portion 52a4) when the suturing device 1 is inserted into the body. The needle accommodation hole may be provided in one of the string support portions 51a and 51a, or may be provided in a projection portion which may be provided separately (for example, in a region between one string support portion and the other string support portion) from the string support portions 51a and 51a.

A through-hole 51d is formed in a joint portion between base end portions of the string support portions 51a and 51a of the front arm 51 such that the through-hole 51d passes through the joint portion in a vertical direction. The guide shaft 51e having substantially a cylindrical shape is fixed to the through-hole 51d such that the guide shaft 51e protrudes to a posterior surface side. The guide shaft 51e is a member which is slidably inserted into a lumen of the back guide portion 52c, and which guides the back arm 52 in reciprocating motion in a central axis direction and rotation. In the embodiment, the guide shaft 51e is made of metal such as stainless steel. The distal end of the front arm moving wire 31 is integrally fixed to a posterior end (end portion facing the proximal end side) of the guide shaft 51e via laser welding or the like.

Figure 4A:
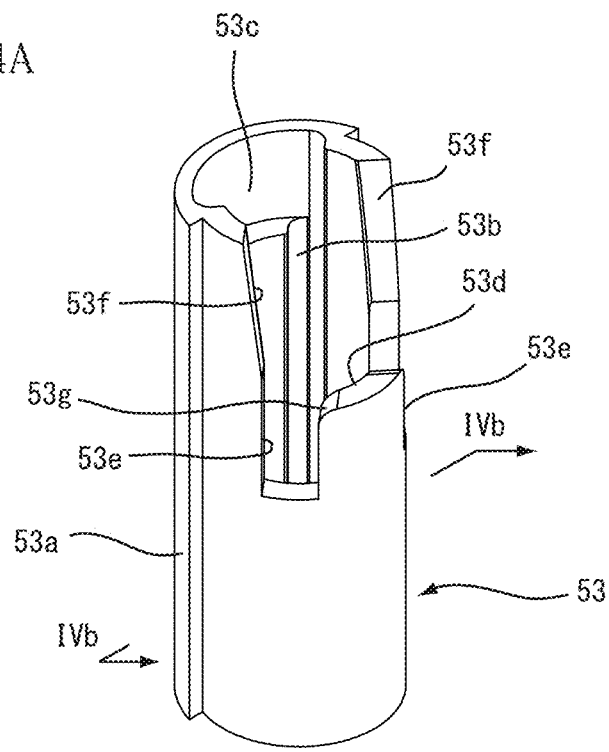
FIG. 4A is a perspective view of a front guide portion of the front arm illustrated in FIG. 3A.
Figure 4B:
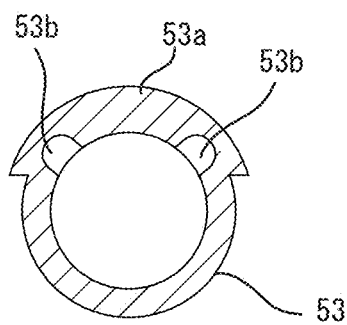
FIG. 4B is a cross-sectional view taken along line IVb-IVb in FIG. 4A.

As illustrated in FIGS. 4A and 4B, the front guide portion 53 is substantially a tubular member. A thick wall portion 53a is formed in part of a back face of the front guide portion 53, and has a wall thickness larger than that of a front face. A pair of recessed guide grooves (first guide groove and second guide groove) 53b and 53b is formed in an inner surface of the thick wall portion 53a such that the pair of recessed guide grooves 53b and 53b extends in the vertical direction (direction substantially parallel to the central axis) and is recessed in a radial direction. Each of the recessed guide grooves 53b and 53b is a portion into which the projection portion 52e formed in the projection member 52d of the back arm 52 is slidably and freely fitted, and which guides the back arm 52 to slide in the central axis direction.

The recessed guide grooves 53b and 53b do not reach an upper portion (posterior end) of the front guide portion 53, and a connection groove 53c, which is recessed in an arc shape, is formed in an upper portion of an inner wall of the front guide portion 53. The connection groove 53c is a portion for allowing the back guide portion 52c (back arm 52) to orbit (rotate) when the back guide portion 52c slides to the proximal end side with respect to a front guide portion 53, and the projection portion 52e becomes located at the position of the connection groove 53c (that is, in a state where the projection portion 52e escapes from the recessed guide grooves 53b and 53b). Both ends (surfaces) of the connection groove 53c are connected to outside portions of inner walls of the recessed guide grooves 53b and 53b, and have the same depth as the depth of the recessed guide grooves 53b and 53b. Incidentally, the recessed guide grooves 53b and 53b reach a lower portion (anterior end) of the front guide portion 53.

A cut-away portion is formed in an upper portion of the front face of the front guide portion 53. Guide through-grooves (first guide groove and second guide groove) 53e and 53e are formed on both sides of a bottom edge portion (edge portion facing an anterior end side) 53d of the cut-away portion such that the guide through-grooves 53e and 53e extend in the vertical direction (direction substantially parallel to the central axis) and pass through the front guide portion 53 from the inside to the outside. Each of the guide through-grooves 53e and 53e is a portion into which the needle support portion 52b of the back arm 52 is slidably and freely fitted, and which guides the back arm 52 in sliding in the central axis direction. Side edge portions on both sides of the guide through-grooves 53e and 53e are surfaces which are substantially parallel to the central axis direction and substantially parallel to each other.

Upper ends (posterior ends) of the guide through-grooves 53e and 53e reach the bottom edge portion 53d of the cut-away portion, and lower ends (anterior ends) of the guide through-grooves 53e and 53e do not reach the lower end (anterior end) of the front guide portion 53. The lower end (anterior end) of each of the guide through-grooves 53e and 53e is set at such position that when the needle support portion 52b of the front arm 51 is fitted into the guide through-grooves 53e and 53e, and reaches the lower ends of the guide through-grooves 53e and 53e, a posterior end of the arrowhead portion 52a4 of the needle-shaped member 52a is capable of passing through either the engagement member 6a or the engagement member 6b of the surgical string 6, and being engaged with either the engagement member 6a or the engagement member 6b.

Posterior parts (which face the proximal end side) of side edge portions on both sides of the cut-away portion of the front guide portion 53 form inclined portions 53f, 53f, respectively. The remaining anterior parts (which face the distal end side) are formed being substantially the same surfaces as those of one side edge portions (both of which are located on the outside) on both sides of the guide through-grooves 53e and 53e. Connection portions between the other side edge portions (both of which are located on the inside) on both sides of the guide through-grooves 53e and 53e and the bottom edge portion 53d are chamfered into arc-shaped chamfered portions 53g, 53g such that the needle support portion 52b is smoothly introduced into the guide through-grooves 53e and 53e. Incidentally, the connection portions are not limited to having an arc shape, and may be inclined surfaces as far as the needle support portion 52b is smoothly introduced into the guide through-grooves 53e and 53e.

The cap 54 is attached to the posterior end of the front guide portion 53. The cap 54 has an arc-shaped recessed portion 54a in which the back guide portion 52c is disposed. The cap 54 is a member that prevents the back arm 52 from escaping from the front arm 51 by being attached to the back end of the front guide portion 53 in a state where the guide shaft 51e is inserted into the back guide portion 52c and the back arm 52 and the front arm 51 are assembled together.

Figure 5A:
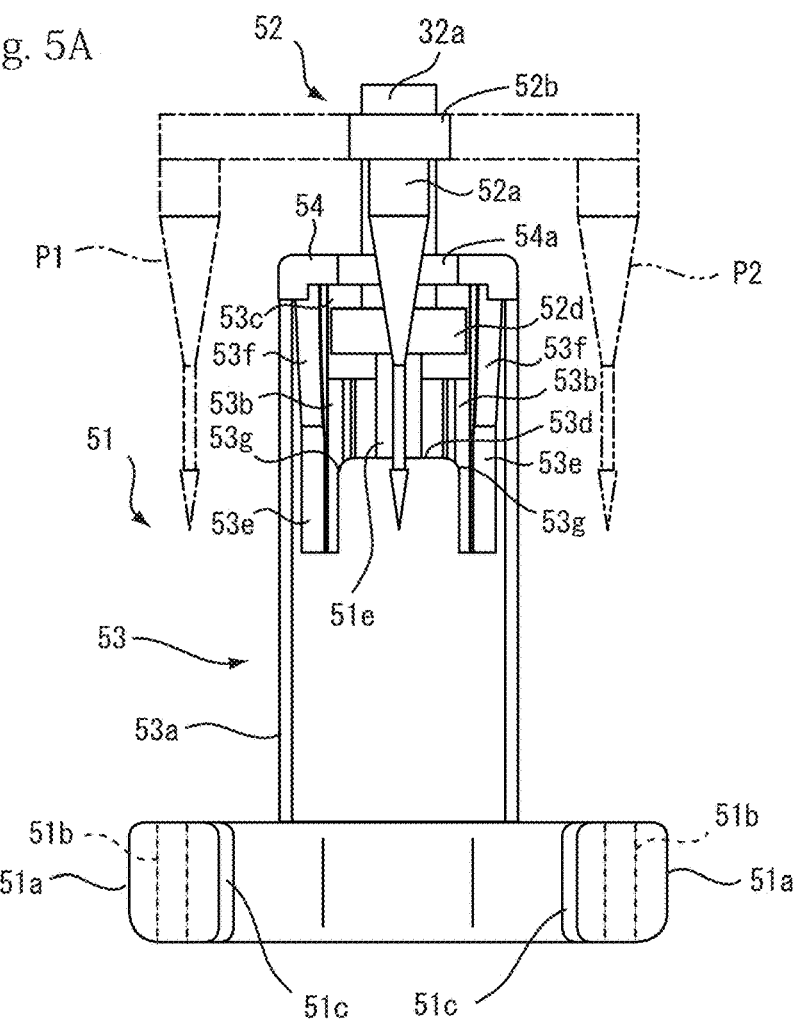
FIG. 5A is a front view for describing how the back arm moves with respect to the front arm, and illustrating a case where the back arm is brought away from the front arm.
Figure 5B:
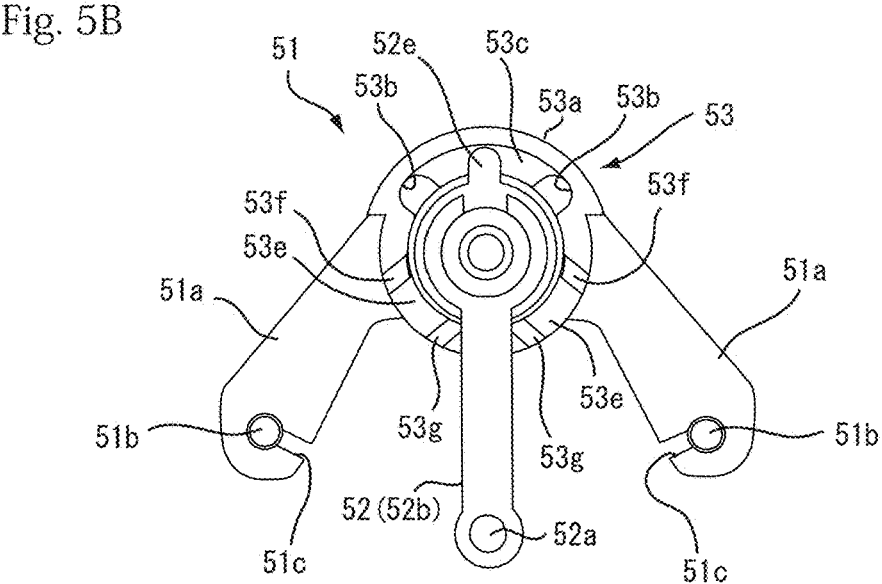
FIG. 5B is a plan view corresponding to the view of FIG. 5A.

Subsequently, a relative motion between the front arm 51 and the back arm 52 will be described with reference to FIGS. 5A, 5B, 6A, 6B, 7A, and 7B. Firstly, as illustrated in FIGS. 5A and 5B, if the back arm 52 has slid away from the front arm 51, the projection member 52d (projection portion 52e) of the back arm 52 becomes located at the position of the connection groove 53c of the front guide portion 53. In this state, the back arm 52 is capable of freely rotating (orbiting) around a central axis of the front arm 51 within a predetermined angular range (substantially 90° in the embodiment) defined by both end surfaces of the connection groove 53c.

Figure 6A:
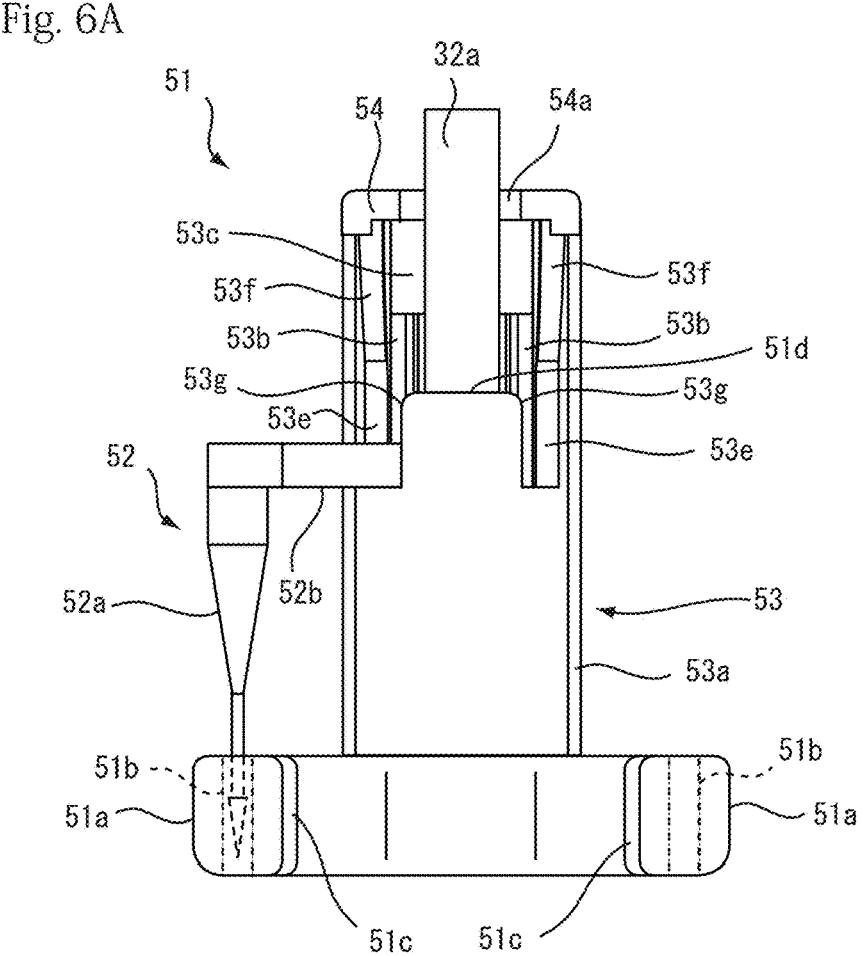
FIG. 6A is a front view for describing how the back arm moves with respect to the front arm, and illustrating a case where a needle-shaped member is positioned in one string support portion and the back arm is brought close to the front arm.
Figure 6B:
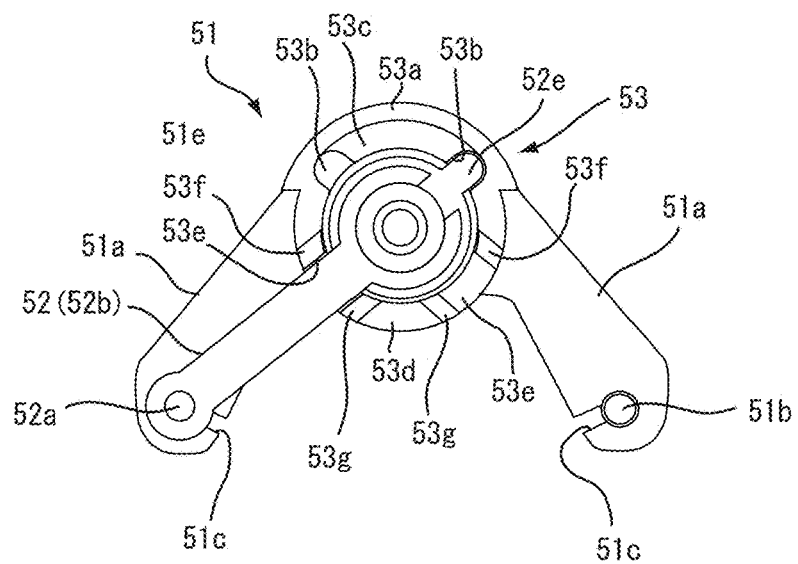
FIG. 6B is a plan view corresponding to the view of FIG. 6A.

In this state, if the back arm 52 rotates as illustrated by the alternate long and short line denoted by reference sign P1 in FIG. 5A (in a clockwise direction in FIG. 5B), the projection portion 52e of the back arm 52 comes into contact with one end surface of the connection groove 53c of the front guide portion 53, thereby restricting the back arm 52 from further rotating in the clockwise direction (refer to FIG. 6B). In this state, if the back arm 52 slides close to the front arm 51, the projection portion 52e moves along one end surface of the connection groove 53c, is led to one recessed guide groove 53b of the front guide portion 53, and is fitted (freely fitted) into the recessed guide groove 53b. The fit between the projection portion 52e and the recessed guide groove 53b is relatively loosely set such that the projection portion 52e is smoothly led to the recessed guide groove 53b. That is, a clearance is set to a relatively large value.

Therefore, the rotation of the back arm 52 with respect to the front arm 51 is restricted, and the back arm 52 is guided along the recessed guide groove 53b in the central axis direction. If the back arm 52 slides further close to the front arm 51, the needle support portion 52b is led to the guide through-groove 53e, and is fitted (freely fitted) into the guide through-groove 53e. The fit between the needle support portion 52b and the guide through-groove 53e is relatively tightly set, as far as not disrupting the sliding, such that the tip of the arrowhead portion 52a4 of the needle-shaped member 52a is accurately led to the through-hole 51b of one string support portion 51a. That is, a clearance is set to a relatively small value.

If the back arm 52 slides further close to the front arm 51, the needle support portion 52b is guided by the guide through-groove 53e, the tip of the arrowhead portion 52a4 of the needle-shaped member 52a is led to the through-hole 51b of one string support portion 51a, and the needle support portion 52b comes into contact with the anterior end of the guide through-groove 53e, and stops. Therefore, as illustrated in FIGS. 6A and 6B, the tip of the arrowhead portion 52a4 of the needle-shaped member 52a becomes located at a predetermined position where the tip of the arrowhead portion 52a4 can be properly engaged with one engagement member 6a (refer to FIG. 1B) of the surgical string 6 supported by the through-hole 51b of one string support portion Ma.

Subsequently, as illustrated by the alternate long and short line denoted by reference sign P1 in FIG. 5A, if the back arm 52 has slid away from the front arm 51, and returns to the original state, the projection member 52d (projection portion 52e) of the back arm 52 becomes located at the position of the connection groove 53c of the front guide portion 53. In this state, if the back arm 52 rotates as illustrated by the alternate long and two short dashes line denoted by reference sign P2 in FIG. 5A (in a counterclockwise direction in FIG. 5B), the projection portion 52e of the back arm 52 comes into contact with the other end surface of the connection groove 53c of the front guide portion 53, thereby restricting the back arm 52 from further rotating in the counterclockwise direction (refer to FIG. 7B). In this state, if the back arm 52 slides close to the front arm 51, the projection portion 52e moves along the other end surface of the connection groove 53c, is led to the other recessed guide groove 53b of the front guide portion 53, and is fitted (freely fitted) into the recessed guide groove 53b. The fit between the projection portion 52e and the recessed guide groove 53b is relatively loosely set such that the projection portion 52e is smoothly led to the recessed guide groove 53b. That is, a clearance is set to a relatively large value.

Therefore, the rotation of the back arm 52 with respect to the front arm 51 is restricted, and the back arm 52 is guided along the recessed guide groove 53b in the central axis direction. If the back arm 52 slides further close to the front arm 51, the needle support portion 52b is led to the guide through-groove 53e, and is fitted (freely fitted) into the guide through-groove 53e. The fit between the needle support portion 52b and the guide through-groove 53e is relatively tightly set, as far as not disrupting the sliding, such that the tip of the arrowhead portion 52a4 of the needle-shaped member 52a is accurately led to the through-hole 51b of the other string support portion 51a. That is, a clearance is set to a relatively small value.

Figure 7A:
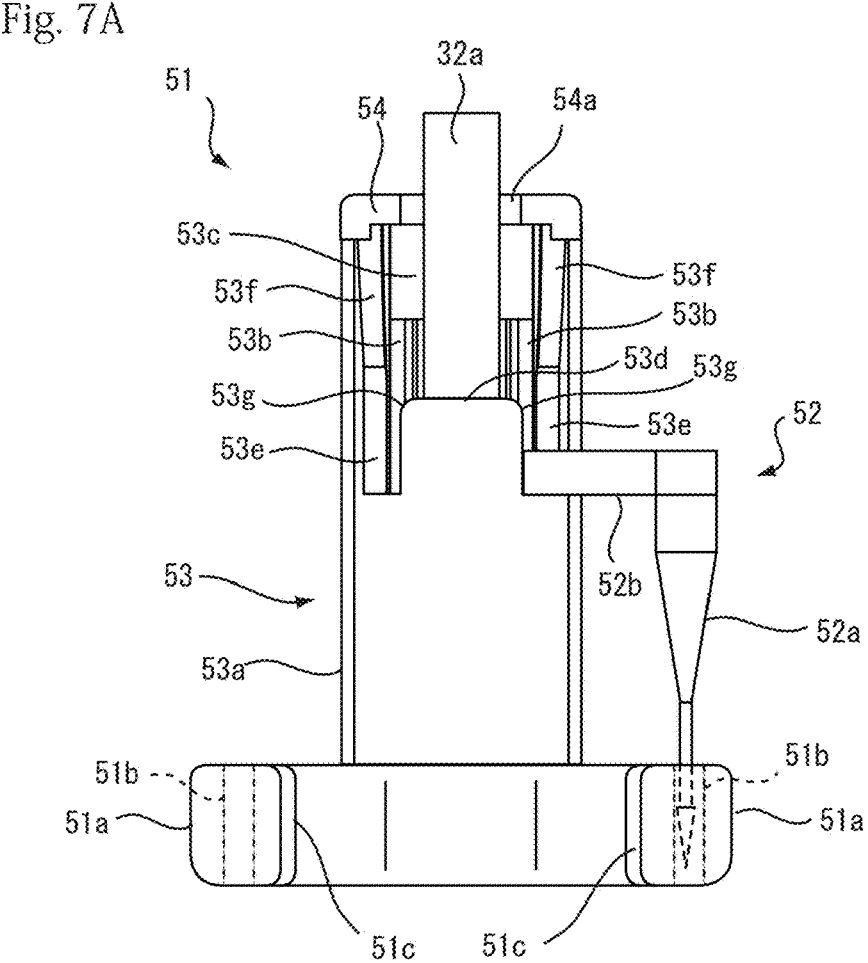
FIG. 7A is a front view for describing how the back arm moves with respect to the front arm, and illustrating a case where the needle-shaped member is positioned in the other string support portion and the back arm is brought close to the front arm.
Figure 7B:
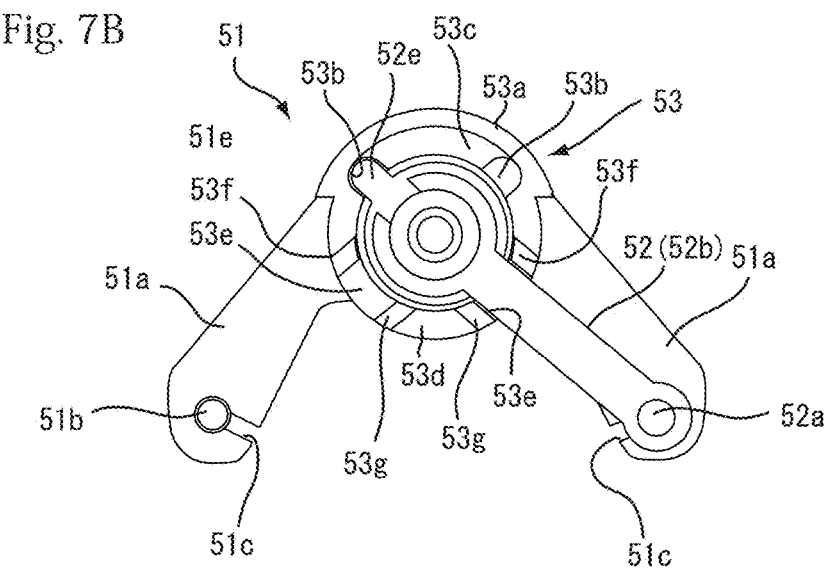
FIG. 7B is a plan view corresponding to the view of FIG. 7A.

If the back arm 52 slides further close to the front arm 51, the needle support portion 52b is guided by the guide through-groove 53e, the tip of the arrowhead portion 52a4 of the needle-shaped member 52a is led to the through-hole 51b of the other string support portion 51a, and the needle support portion 52b comes into contact with the front end of the guide through-groove 53e, and stops. Therefore, as illustrated in FIGS. 7A and 7B, the tip of the arrowhead portion 52a4 of the needle-shaped member 52a becomes located at a predetermined position where the tip of the arrowhead portion 52a4 can be properly engaged with the other engagement member 6b (refer to FIG. 1B) of the surgical string 6 which is in the through-hole 51*b* of the other string support portion 51*a* and supported by the through-hole 51*b*.

As described above, in the embodiment, if the back arm 52 slides in a direction (first direction) in which the back arm 52 becomes close to the front arm 51, the projection portion 52*e* is guided by the recessed guide groove 53*b*, and further, the needle support portion 52*b* is guided by the guide through-groove 53*e*. Therefore, the tip of the arrowhead portion 52*a*4 of the needle-shaped member 52*a* is accurately led to the predetermined position where the tip of the arrowhead portion 52*a*4 can be properly engaged with the engagement members 6*a* and 6*b* of the surgical string 6 which is in the through-hole 51*b* of the string support portion 51*a* and supported by the through-hole 51*b*. As a result, when the back arm 52 is brought close to the front arm 51, the rotational position of the back arm 52 is effectively prevented from being misaligned with that of the front arm 51. For this reason, there is no need to realign the positions as in the related art, and it is possible to promptly perform suture treatment.

Since the embodiment employs both a relatively loose guide structure, which is applied between the recessed guide grooves 53*b* and 53*b* and the projection portion 52*e*, and a relatively precise guide structure applied between the guide through-grooves 53*e* and 53*e* and the needle support portion 52*b*, it is possible to provide a smooth guide as a whole. If only the relatively precise guide structure applied between the guide through-grooves 53*e* and 53*e* and the needle support portion 52*b* is employed, since the clearance between each of the guide through-grooves 53*e* and 53*e* and the needle support portion 52*b* is small, the needle support portion 52*b* may not be smoothly introduced into the guide through-grooves 53*e* and 53*e*. However, as in the embodiment, if the relatively loose guide structure applied between the recessed guide grooves 53*b* and 53*b* and the projection portion 52*e* is added, it is possible to solve the problem, and to realize a smooth guide as a whole.

However, the relatively loose guide structure applied between the recessed guide grooves 53*b* and 53*b* and the projection portion 52*e* may be omitted, and only the relatively precise guide structure applied between the guide through-grooves 53*e* and 53*e* and the needle support portion 52*b* may be employed. Further, the guide structure applied between the guide through-grooves 53*e* and 53*e* and the needle support portion 52*b* may be omitted, and only the guide structure applied between the recessed guide grooves 53*b* and 53*b* and the projection portion 52*e* may be employed. In this case, the clearance between each of the recessed guide grooves 53*b* and 53*b* and the projection portion 52*e* may be set to a relatively small value. A single guide structure may be inferior to a combination of both guide structures from the viewpoint of guiding smoothness, but the single guide structure is capable of simplifying the structure of the device.

(Operation Unit)

The operation unit (handle) 4 of the suturing device 1 has a configuration as illustrated in FIG. 1A. That is, the operation unit 4 includes a slider portion 41 and a base portion 42. The slider portion 41 is slidably provided in the base portion 42. The slider portion 41 is capable of moving with respect to the base portion 42 between two positions, specifically, a position where the slider portion 41 has moved to a tip (distal end) and a position where the slider portion 41 has moved to a base (proximal end).

Specifically, a cylindrical portion 41*a* is substantially cylindrically formed at a distal end of the slider portion 41. A grip member 41*b* is provided at a proximal end of the slider portion 41, and a distal end of the grip member 41*b* is fixed to the cylindrical portion 41*a*. The cylindrical portion 41*a* of the slider portion 41 is provided with a wire insertion hole (not illustrated) which has substantially a cylindrical shape, opens at a distal end of the cylindrical portion 41*a*, and extends along an axial line of the cylindrical portion 41*a*. Part of the proximal end of the front arm moving wire 31 is connected and fixed to the cylindrical portion 41*a* of the slider portion 41.

The base portion 42 is substantially a tubular member which is obtained by joining together a pair of substantially symmetric halved members using a plurality of screws or the like (not illustrated). The base portion 42 has a slider portion insertion hole (not illustrated) having substantially a cylindrical shape, which opens at a proximal end of the base portion 42 and extends along an axial line of the base portion 42. If the cylindrical portion 41*a* of the slider portion 41 is inserted into the slider portion insertion hole, the slider portion 41 is attached to the base portion 42 such that the slider portion 41 is capable of sliding along the axial line of the base portion 42 and rotating around an axis of the base portion 42.

Further, the base portion 42 has a tube insertion hole (not illustrated) having substantially a cylindrical shape, which opens at a distal end of the base portion 42 and extends along the axial line of the base portion 42. The proximal end of the back arm moving tube 32 is inserted into the tube insertion hole, and part of the proximal end of the posterior arm moving tube 32 is connected and fixed to the base portion 42.

(Suturing Step)

Hereinbelow, a suturing step (suture procedure) of suturing an incised site using the suturing device 1 will be described with reference to FIGS. 8A to 8K. Incidentally, hereinbelow, as an example, there is described a case where an incised site formed in the stomach wall is sutured.

Firstly, an operator inserts the shaft of the endoscope 2, to which the suturing device 1 is attached, into the stomach, and disposes the suturing unit 5 of the suturing device 1 in the vicinity of an incised site to be sutured. Subsequently, as illustrated in FIG. 1B, the operator brings the back arm 52 away from the front arm 51 by operating the operation unit 4.

Figure 8A:
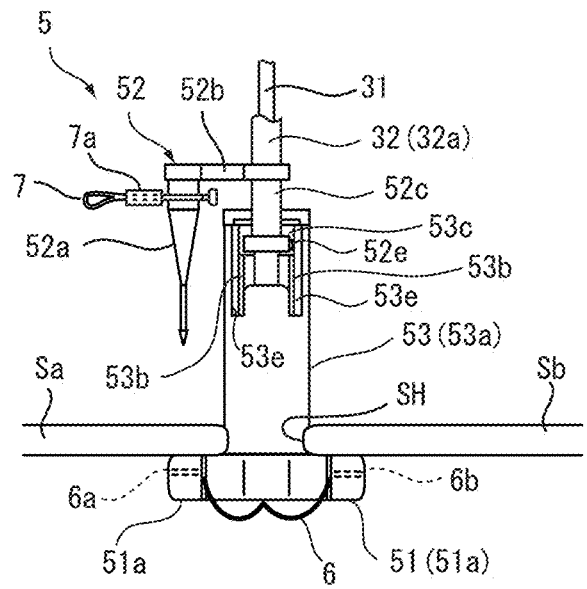
FIG. 8A is a view illustrating the sequence of procedures (suture) which are performed using the suturing device in the embodiment of the invention, and illustrating a first step.

In this state, the operator executes a first step illustrated in FIG. 8A. In the first step illustrated in FIG. 8A, firstly, as illustrated in the same drawing, the operator inserts only the front arm 51, which is disposed away from the back arm 52, into an incised site SH by pushing the entirety of the operation unit 4 into the case tube 33 to the distal end side, and rotating the operation unit 4 as necessary. Before and after taking the foregoing action, the operator disposes the front arm 51 and the back arm 52 by rotating the back arm 52 with respect to the front arm 51, such that one aperture edge portion Sa of the incised site SH is interposed between one string support portion 51*a* of the front arm 51 and the needle-shaped member 52*a* (arrowhead portion 52*a*4).

Figure 8B:
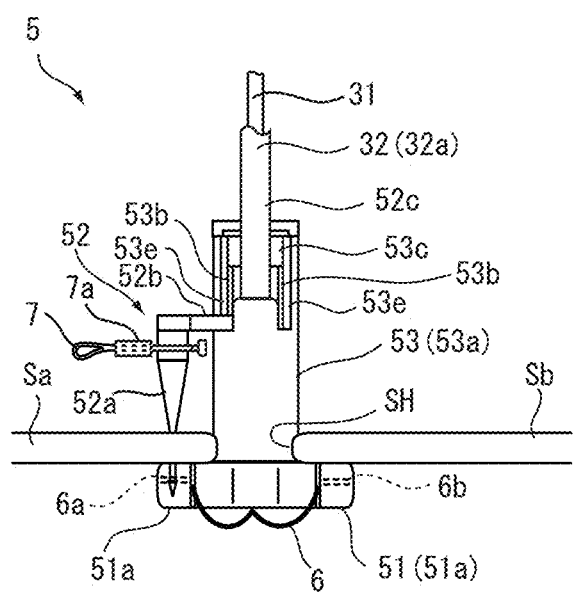
FIG. 8B is a view illustrating a second step subsequent to the step of FIG. 8A.

Subsequently, if the operator brings the front arm 51 close to the back arm 52, as illustrated in FIG. 8B, the needle-shaped member 52*a* punctures one aperture edge portion Sa and passes through the aperture edge portion Sa, and further, the arrowhead portion 52*a*4 of the needle-shaped member 52*a* passes through the through-hole of the engagement member 6*a* which is accommodated (supported) in the accommodation space of one string support portion 51*a*. Therefore, the through-hole of the engagement member 6*a* reaches the small-diameter portion 52*a*3 of the needle-shaped member 52*a*, and the engagement member 6*a* becomes engaged with the needle-shaped member 52*a*.

Figure 8C:
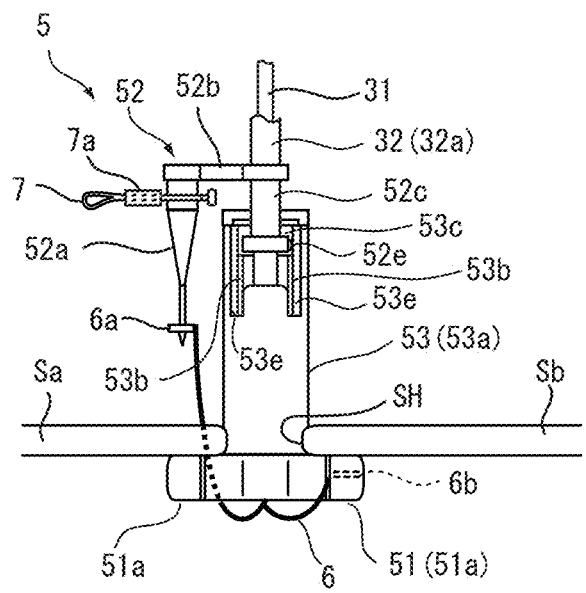
FIG. 8C is a view illustrating a third step subsequent to the step of FIG. 8B.

Subsequently, if the operator brings the front arm 51 away from the back arm 52 in the suturing unit 5 by operating the operation unit 4, as illustrated in FIG. 8C, the needle-shaped member 52*a*, with which the engagement member 6*a* is engaged, returns backward into the stomach through a hole (hereinbelow, referred to as a first puncture hole) which is formed when the needle-shaped member 52*a* is inserted through one aperture edge portion Sa. Therefore, part (part of the engagement member 6*a*) of the surgical string 6 has passed through one aperture edge portion Sa.

Figure 8D:
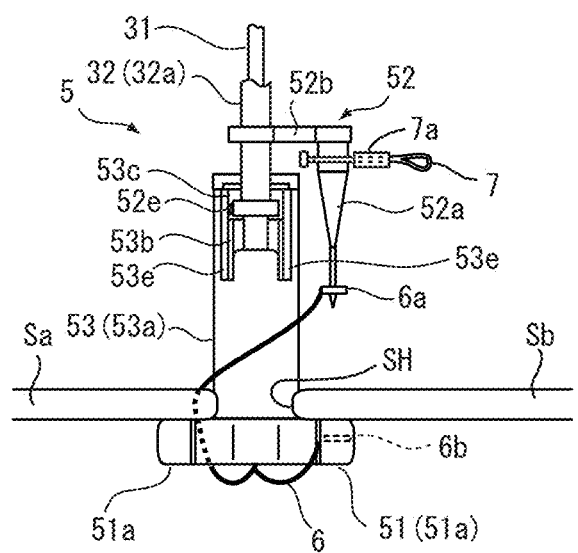
FIG. 8D is a view illustrating a fourth step subsequent to the step of FIG. 8C.

Thereafter, as illustrated in FIG. 8D, the operator disposes the front arm 51 and the back arm 52 such that the other aperture edge portion Sb of the incised site SH is interposed between the other string support portion 51*a* of the front arm 51 and the needle-shaped member 52*a*.

Figure 8E:
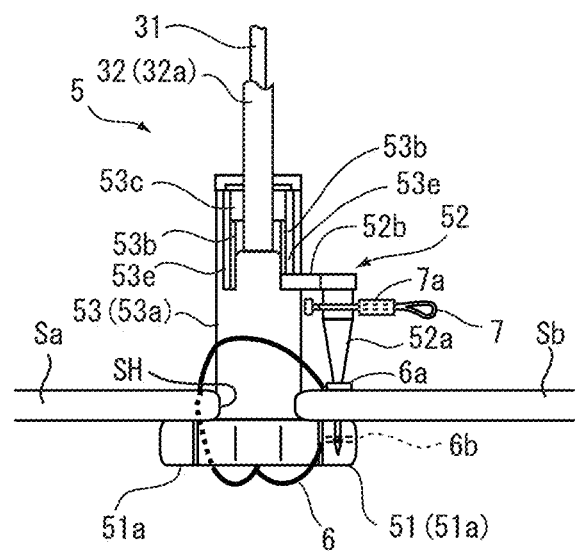
FIG. 8E is a view illustrating a fifth step subsequent to the step of FIG. 8D.

In this state, if the operator brings the back arm 52 close to the front arm 51 by operating the operation unit 4, as illustrated in FIG. 8E, the needle-shaped member 52*a* punctures the other aperture edge portion Sb and passes through the aperture edge portion Sb, and further, the arrowhead portion 52*a*4 of the needle-shaped member 52*a* passes through the through-hole of the engagement member 6*b* which is accommodated (supported) in the accommodation space of the other string support portion 51*a*. Therefore, the through-hole of the engagement member 6*b* reaches the small-diameter portion 52*a*3 of the needle-shaped member 52*a*, and the engagement member 6*b* becomes engaged with the needle-shaped member 52*a*.

Figure 8F:
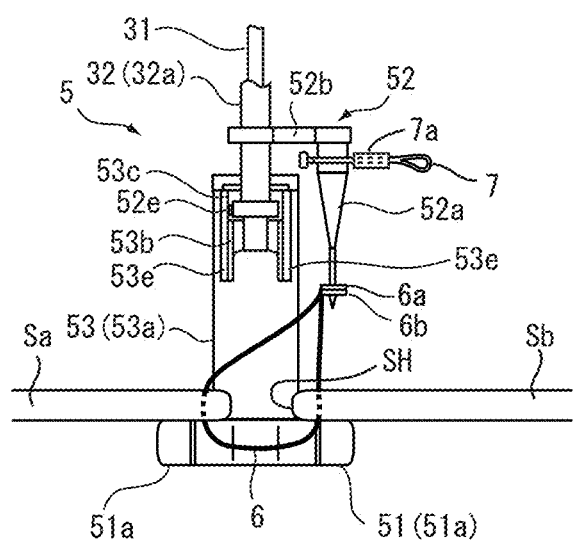
FIG. 8F is a view illustrating a sixth step subsequent to the step of FIG. 8E.

Subsequently, if the operator brings the front arm 51 away from the back arm 52 by operating the operation unit 4, as illustrated in FIG. 8F, the needle-shaped member 52*a*, with which the engagement member 6*b* is engaged, returns backward into the stomach through a hole (hereinbelow, referred to as a second puncture hole) which is formed when the needle-shaped member 52*a* is inserted through the other aperture edge portion Sb. Therefore, part (part of the engagement member 6*b*) of the surgical string 6 has passed through the other aperture edge portion Sb.

Therefore, both of a pair of the engagement members 6*a* and 6*b*, to which both ends of the surgical string 6 are fixed, respectively, are engaged with the single needle-shaped member 52*a*, and a ring is formed by the surgical string 6 which passes through the first puncture hole from the needle-shaped member 52*a* (that is, inside the stomach) to the outside of the stomach, and returns through the second puncture hole from the outside of the stomach to the needle-shaped member 52*a* (that is, inside the stomach).

Figure 8G:
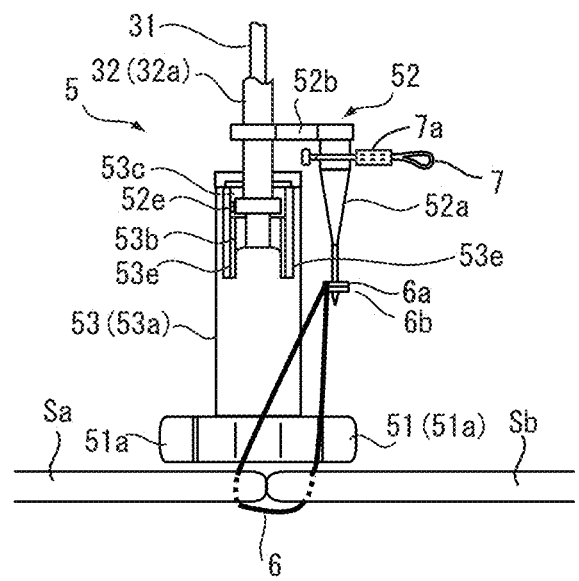
FIG. 8G is a view illustrating a seventh step subsequent to the step of FIG. 8F.

Subsequently, as illustrated in FIG. 8G, the operator moves the front arm 51 (string support portion 51*a*) into the stomach through the incised site SH by operating the operation unit 4. If the front arm 51 (string support portion 51*a*) enters the stomach, since the needle-shaped member 52*a* moves away from the incised site SH, and both ends of the surgical string 6 moves away from the incised site SH, parts of the surgical string 6, which pass through the first puncture hole and the second puncture hole, are pulled close to each other, and end surfaces of a pair of the aperture edge portions Sa and Sb of the incised site SH come into contact with each other, and are joined together.

Figure 8H:
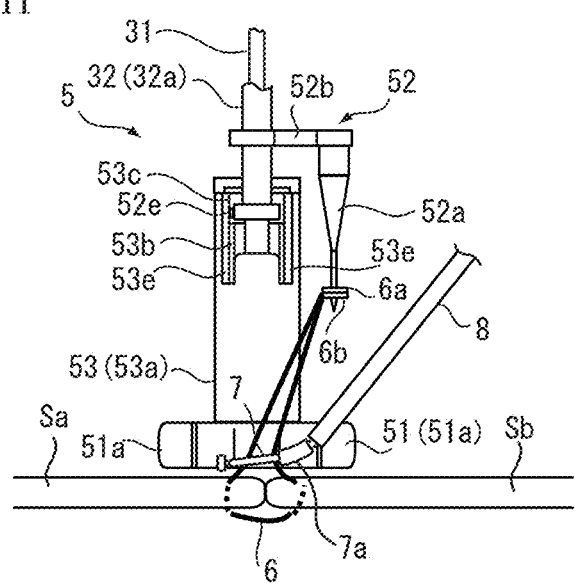
FIG. 8H is a view illustrating an eighth step subsequent to the step of FIG. 8G.

If the operator finishes the procedure of suturing the incised site SH using the suturing device 1, subsequently, the operator ties the surgical string 6. A tying device 8 illustrated in FIG. 8H is used for the procedure. As the tying device 8, for example, it is possible to use a device including a sheath that is introduced into a lumen through a treatment tool guide tube of an endoscope; and an operation wire that is slidably inserted into the sheath, in which a connection hook is provided at a distal end of the operation wire such that the connection hook opens legs in substantially a V shape due to elasticity thereof when protruding from a distal end of the sheath, and closes the legs when being pulled into a distal end portion of the sheath.

As illustrated in FIG. 8G, since the tying tool 7 is held by the base end portion (large-diameter portion 52*a*1) of the needle-shaped member 52*a* in a state where the tying loop 7*c* (refer to FIG. 1B) is inserted into the base end portion, the operator connects the tying tool 7 to the distal end of the sheath of the tying device 8 by disposing a distal end of the tying device 8 (refer to FIG. 8H) in the vicinity of the connection loop 7*b* of the tying tool 7, grasping the connection loop 7*b* using the connection hook, which has protruded from the tying device 8 and opened the legs, and pulling the connection loop 7*b* into the distal end portion of the sheath of the tying device 8.

Subsequently, as illustrated in FIG. 8H, the operator inserts both end portions of the surgical string 6 into the tying loop 7*c* of the tying tool 7 by moving the distal end portion of the sheath of the tying device 8, to which the tying tool 7 is connected, to the incised site SH (downward in FIG. 8H). Therefore, the surgical string 6 is squeezed, and both end portions of the surgical string 6 are bundled.

Figure 8I:
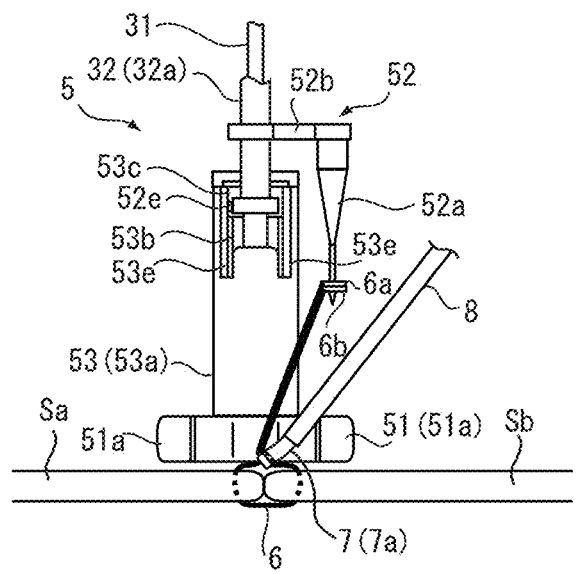
FIG. 8I is a view illustrating a ninth step subsequent to the step of FIG. 8H.

In a state where both end portions of the surgical string 6 are bundled, if the operator slides the operation wire such that the connection hook of the tying device 8 is further pulled into the sheath, as illustrated in FIG. 8I, the tying loop 7*c* together with the surgical string 6 is pulled into the tightening tube 7*a*, and the tying loop 7*c* and the surgical string 6 are accommodated in the tightening tube 7*a* in a state where the tying loop 7*c* and the surgical string 6 are in close contact with each other and are compressed. That is, since the tying loop 7*c* and the surgical string 6 are accommodated in the tube 7*a* in a state where the tying loop 7*c* and the surgical string 6 are interference fitted into the tube 7*a*, the surgical string 6 and one end portion of the tying loop 7*c* are fixed not to fall out of the tube 7*a*. As a result, the tying of the surgical string 6 is completed.

Figure 8J:
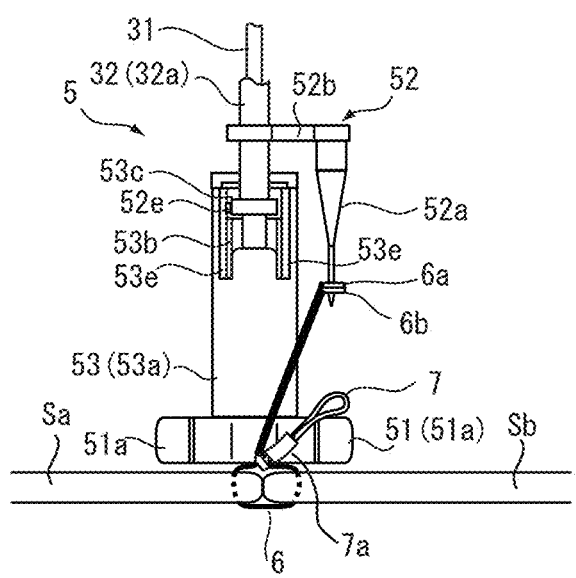
FIG. 8J is a view illustrating a tenth step subsequent to the step of FIG. 8I.

When the tying of the surgical string 6 is completed, if while not changing the position of the tying wire, the operator slides the sheath to the proximal end side such that the operation wire of the tying device 8 is pulled into the sheath, the connection hook and the other end portion of the loop member protrude (are exposed) from the distal end of the sheath of the tying device 8, the connection hook opens the legs due to elasticity thereof, the grasping is released, and as illustrated in FIG. 8J, the tying device 8 becomes separate from the tying tool 7 in a tied state.

Figure 8K:
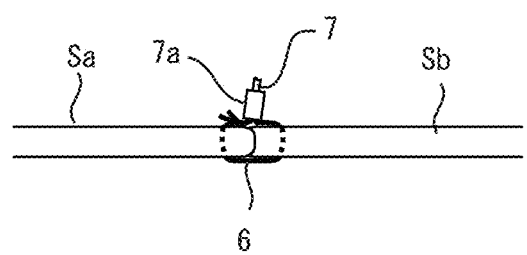
FIG. 8K is a view illustrating a final step subsequent to the step of FIG. 8J.

Finally, as illustrated in FIG. 8K, the operator detaches the tying tool 7 and the suturing unit 5 from each other by cutting the surgical string 6 between the tying tool 7 and the suturing unit 5 (needle-shaped member 52*a*) using scissor forceps for an endoscope which is called a loop cutter, or the like, and supplementally as necessary, cuts the other end portion of the loop member of the tying tool 7 in a tied state using the loop cutter or the like, and recovering the cut away portion. As a result, a series of suture procedures using a single needle is completed.

The embodiment has been exemplarily described to help easy understanding of the invention, and is not intended to limit the invention. Therefore, each element disclosed in the embodiment is intended to include all design changes or equivalents which fall within the technical scope of the invention.

EXPLANATIONS OF LETTERS OR NUMERALS

1 SUTURING DEVICE
2 ENDOSCOPE
3 SHEATH UNIT
  31 FRONT ARM MOVING WIRE
  32 BACK ARM MOVING TUBE
  33 CASE TUBE
4 OPERATION UNIT
  41 SLIDER PORTION
  42 BASE PORTION
5 SUTURING UNIT
  51 FRONT ARM
    51a STRING SUPPORT PORTION
  52 BACK ARM
    52a NEEDLE-SHAPED MEMBER
      52a4 ARROWHEAD PORTION
    52b NEEDLE SUPPORT PORTION
    52c BACK GUIDE PORTION
    52d PROJECTION MEMBER
    52e PROJECTION PORTION
  53 FRONT GUIDE PORTION
    53a THICK WALL PORTION
    53b RECESSED GUIDE GROOVE (FIRST GUIDE GROOVE AND SECOND GUIDE GROOVE)
    53c CONNECTION GROOVE
    53d BOTTOM EDGE PORTION
    53e GUIDE THROUGH-GROOVE (FIRST GUIDE GROOVE AND SECOND GUIDE GROOVE)
    53f INCLINED PORTION
    53g CHAMFERED PORTION
  54 CAP
6 SURGICAL STRING
  6a, 6b ENGAGEMENT MEMBER
7 TYING TOOL
  7a TIGHTENING TUBE
  7b CONNECTION LOOP
  7c TYING LOOP
SH INCISED SITE
Sa, Sb APERTURE EDGE PORTION
8 TYING DEVICE

The invention claimed is:

1. A suturing device for being inserted into and used in a body, the device comprising:

a front arm having a string support portion supporting both ends of a surgical string, and a front guide portion attached to the string support portion; and a back arm having a needle-shaped member, a needle support portion supporting the needle-shaped member in a state of pointing to a predetermined first direction, and a back guide portion attached to the front guide portion such that the back guide portion is capable of sliding in a direction substantially parallel to the first direction, and rotating around an axis substantially parallel to the first direction, wherein the front guide portion has a substantially tubular member, wherein the back guide portion is disposed inside the front guide portion, wherein the front guide portion has a first guide groove guiding the needle-shaped member to one end of the surgical string supported by the string support portion, and a second guide groove guiding the needle-shaped member to the other end of the surgical string, when the back arm slides in the first direction, wherein the first guide groove and the second guide groove each has a guide through-groove which extends in the direction substantially parallel to the first direction, and which is formed in a wall portion of the front guide portion such that the guide through-grooves extend from an inside to an outside of the tubular member, and wherein the needle support portion is slidably and freely fitted into the guide through-grooves.

2. The suturing device according to claim 1, wherein the first guide groove and the second guide groove each is a recessed guide groove which extends in the direction substantially parallel to the first direction, and which is formed in an inner wall of the front guide portion, and wherein the back guide portion is provided with a projection portion that is freely fitted into the recessed guide grooves.

3. The suturing device according to claim 2, wherein a tying tool, which is capable of tying the surgical string with which an internal body tissue is sutured, is mounted on the needle-shaped member.

4. The suturing device according to claim 1, wherein a tying tool, which is capable of tying the surgical string with which an internal body tissue is sutured, is mounted on the needle-shaped member.

* * * * *